(12) United States Patent
Huang et al.

(10) Patent No.: US 12,036,543 B2
(45) Date of Patent: Jul. 16, 2024

(54) PREPARATION METHOD OF DOPED ZnO CATALYST AND SYNTHESIS METHOD OF HIGHER ALCOHOL USING SAME

(71) Applicant: Taiyuan University of Technology, Taiyuan (CN)

(72) Inventors: Wei Huang, Taiyuan (CN); Fang Li, Taiyuan (CN); Qian Zhang, Taiyuan (CN); Penglong Jia, Taiyuan (CN); Yongjun Liu, Taiyuan (CN)

(73) Assignee: Taiyuan University of Technology, Taiyuan (CN)

( * ) Notice: Subject to any disclaimer, the term of this patent is extended or adjusted under 35 U.S.C. 154(b) by 0 days.

(21) Appl. No.: 17/977,514

(22) Filed: Oct. 31, 2022

(65) Prior Publication Data

US 2023/0138719 A1 May 4, 2023

(30) Foreign Application Priority Data

Nov. 4, 2021 (CN) .......................... 202111300875.X

(51) Int. Cl.
| | | |
|---|---|---|
| *B01J 37/03* | (2006.01) | |
| *B01J 23/06* | (2006.01) | |
| *B01J 23/08* | (2006.01) | |
| *B01J 23/80* | (2006.01) | |
| *B01J 37/08* | (2006.01) | |

(52) U.S. Cl.
CPC .............. *B01J 37/033* (2013.01); *B01J 23/06* (2013.01)

(58) Field of Classification Search
CPC . B01J 37/033; B01J 23/06; B01J 23/08; B01J 23/80; B01J 37/08

USPC .................. 502/343, 342; 518/713
See application file for complete search history.

(56) References Cited

U.S. PATENT DOCUMENTS

| | | | | |
|---|---|---|---|---|
| 2013/0168328 A1* | 7/2013 | Bagabas | ................... | C09C 1/02 |
| | | | | 502/343 |
| 2014/0141968 A1* | 5/2014 | Wu | ...................... | B01D 53/885 |
| | | | | 502/343 |

FOREIGN PATENT DOCUMENTS

| | | | | | |
|---|---|---|---|---|---|
| CN | 109126808 A | * | 1/2019 | .............. | B01J 23/80 |
| CN | 109621965 A | * | 4/2019 | .............. | B01J 23/80 |
| WO | WO-2021262922 A1 | * | 12/2021 | .............. | B01J 21/04 |

* cited by examiner

*Primary Examiner* — Patricia L. Hailey
(74) *Attorney, Agent, or Firm* — Notaro, Michalos & Zaccaria P.C.

(57) ABSTRACT

The present disclosure provides a preparation method of a doped ZnO catalyst. The preparation method includes the following steps: mixing a precipitant and a first solvent to form a first solution having 1 mol/L to 5 mol/L of the precipitant by concentration; mixing one of a Cu salt or a Ga salt, a Zn salt, and a second solvent to form a second solution having Cu and Zn at a molar ratio of less than 0.05:1 and Ga and Zn at a molar ratio of less than 0.1:1; subjecting the first solution and the second solution to precipitation or hydrolysis at 50° C. to 90° C. to obtain a precipitate, and washing and drying the precipitate to obtain a precursor sample; and conducting calcination on the precursor sample at 300° C. to 500° C. for 3 h to 5 h to obtain a Cu-doped ZnO catalyst or a Ga-doped ZnO catalyst.

20 Claims, No Drawings

PREPARATION METHOD OF DOPED ZnO CATALYST AND SYNTHESIS METHOD OF HIGHER ALCOHOL USING SAME

CROSS REFERENCE TO RELATED APPLICATION

This patent application claims the benefit and priority of Chinese Patent Application No. 202111300875.X, filed with the China National Intellectual Property Administration on Nov. 4, 2021, the disclosure of which is incorporated by reference herein in its entirety as part of the present application.

TECHNICAL FIELD

The present disclosure relates to the technical field of catalysis and chemical industry, in particular to a preparation method of a doped ZnO catalyst and a synthesis method of a higher alcohol using same.

BACKGROUND

Energy is an important material basis for the survival and development of human society. The development and utilization of energy has greatly promoted the development of the world economy and human society. As basic substances, carbon monoxide (CO) and hydrogen in synthesis gas come from a wide range of sources. The conversion of coal or natural gas into syngas has become a mature technology in industry, and the synthesis of low-carbon mixed alcohols from the synthesis gas is a highly popular research topic in the field of $C_1$ chemistry. Synthesis gas-to-low-carbon alcohol technology is to synthesize low-carbon mixed alcohols dominated by $C_1$-$C_6$ under the action of a heterogeneous catalyst from the synthesis gas, among which alcohols containing two or more carbon atoms are called higher alcohols. Higher alcohols have broad application prospects, and can prepare alcohols with a higher industrial value by separation. In addition, higher alcohols can be widely used as alternative liquid fuels, gasoline additives, as well as important chemical intermediates. Synthesis gas from non-petroleum carbon resources can be transformed into higher alcohols through indirect routes suffer from multiple processes and energy-consuming. While the direct route attracted most interest due to its low production cost, atomic economy, and strong operational feasibility. The technology of preparing higher alcohols from the synthesis gas has opened up a diversified product route for producing oxygen-containing liquid fuels, oil additives, and high value-added alcohol chemicals based on coal-based synthesis gas through non-petroleum routes. The technology is more economical than current methanol synthesis technologies, and can be implemented gradually to replace the methanol synthesis technologies in production of high value-added fuel alcohols or chemical alcohols. The technology has broad prospects for use in effectively solving methanol overproduction, avoiding methanol market risks, and producing alternative fuels. After the implementation of industrial production, this technology may form an industrial chain that synthesizes alternatives to fossil fuels and chemical alcohols using coal as a source through the non-petroleum routes. As a result, more employment opportunities can be created to promote the development of industries such as secondary processing of related alcohol chemicals.

At present, a variety of catalyst systems for the synthesis of higher alcohols have been developed, which are roughly divided into four categories: (1) Fischer-Tropsch (F-T) synthesis catalysts, with straight-chain mixed alcohols as a main product. However, F-T catalysts has the disadvantages of high hydrocarbon selectivity, wide carbon number distribution, and easy carbon deposition; (2) Mo-based catalysts has the advantages of its sulfur resistance, coking resistance, high catalytic activity and low cost. The disadvantage is that the product contains sulfur and the reaction requires high pressure; (3) Rh based catalysts is the only single metal catalyst that can selectively hydrogenate CO to produce higher alcohols. However, its high cost limits its application in large-scale syngas conversion process; (4) Modified methanol-based synthesis catalysts can be roughly divided into two categories: 1) low temperature copper based catalysts (i.e., Cu—ZnO—$Al_2O_3$, Cu/$ZrO_2$, Cu/$CeO_2$, etc.) and 2) high temperature chromium based catalysts (e.g., Zn—Cr mixed oxides) The most studied catalyst for low temperature low carbon alcohol synthesis is based on Cu and ZnO with reaction conditions at generally 220° C. to 290° C. and 4 MPa to 6 MPa. $Al_2O_3$ or $Cr_2O_3$ is usually used as a structural accelerator to increase the surface area and prevent sintering. The direct route in mild condition through non-noble metal promoted Cu/ZnO based catalysts attracted most interest due to its lower energy consumption, simple preparation process, a low price, mild reaction conditions, a high reactivity and total alcohol selectivity. It is generally believed that Cu—Zn-based catalysts are bifunctional catalysts. These Cu—Zn-based catalysts have the active component copper with a loading of not less than 10 wt %, while having an extremely low proportion of the higher alcohols at a copper-zinc ratio of 1:1. Alkali metals such as Li, K, Cs neutralized surface acid centers, enhanced the coupling of C—C and C—O, and provided basic sites to improve the selectivity of higher alcohols. Transition metals such as Co, Fe, La, Mn, Ce enhanced the dispersibility of copper, increased the reducibility of the active phase and accelerated the growth of the carbon chain. Methanol and isobutanol is the main product in previous literatures, and the reaction always suffers from low yield as well as low selectivity.

In summary, the catalytic product of Cu/ZnO catalyst is mainly methanol, and the copper component content of not less than 10 wt % with a very low proportion of higher alcohols. In a catalyst with a higher selectivity of the higher alcohols, Fischer-Tropsch element or alkali metals is added on the basis of a copper-zinc component.

SUMMARY

A purpose of the present disclosure is to provide a preparation method of a Cu-doped ZnO catalyst or a Ga-doped ZnO catalyst capable of synthesizing a higher alcohol, and a synthesis method of a higher alcohol using a doped ZnO catalyst. The higher alcohol has a relatively high proportion and does not use any Fischer-Tropsch element.

In the present disclosure, it is found that there is no report on synthesis gas in production of the higher alcohols using the Ga-doped ZnO catalyst, and there is no report on the doped ZnO catalyst using low-loaded Cu in synthesizing the higher alcohols. Therefore, a ZnO catalyst is electronically controlled using the Cu-doped ZnO catalyst or the Ga-doped ZnO catalyst to synthesize the higher alcohols on the ZnO catalyst.

In an example of the present disclosure, the prepared Cu-doped ZnO catalyst or Ga-doped ZnO catalyst has an extremely low metal content, and does not use any additives or Fischer-Tropsch elements, which exhibits a high activity and an excellent proportion of the higher alcohols in hydrogenation of CO, with a stronger synergistic effect of copper-zinc or gallium-zinc. The catalyst synthesis method is relatively simple, and metal copper or gallium is doped into the crystal lattice of ZnO by co-precipitation or hydrothermal synthesis. The synthesized catalyst has a uniform flower-like or nano-sheet shape, where 1 mol of the ZnO has a Cu doping amount of 1 mol % to 4 mol % and a Ga doping amount of 1 mol % to 10 mol %.

In an example of the present disclosure, the preparation method of the catalyst has a simple process, a low cost, and a high catalytic performance, which conforms to a development trend of green chemical industry; moreover, the preparation method has broad prospects for use in the field of catalytic conversion of CO into important chemicals.

The present disclosure provides a preparation method of a Cu-doped ZnO catalyst or a Ga-doped ZnO catalyst for synthesizing a higher alcohol on a fixed bed, and use thereof. In the present disclosure, on the basis of a current research progress of synthesis gas in preparing higher alcohol catalysts, a new type of Cu-doped ZnO catalyst or a Ga-doped ZnO catalyst is designed without any additives or Fischer-Tropsch elements using ZnO as a main active component of the catalyst by doping an extremely small amount of copper or gallium to enhance an interaction between the ZnO and the Cu or Ga. Compared with traditional Cu/ZnO catalysts, the Cu-doped ZnO catalyst has a lower copper content, and copper ions enter the crystal lattice of ZnO. Through the preparation method, a new type of higher alcohol catalyst can be prepared with simple components, easy operations, a desirable catalyst activity, an extremely-high proportion of the higher alcohols, and a satisfying catalytic efficiency.

In one aspect of the present disclosure, a Cu-doped ZnO catalyst or a Ga-doped ZnO catalyst is provided for preparing a higher alcohol by hydrogenation of CO on a fixed bed; and the catalyst can be prepared by co-precipitation or hydrothermal synthesis, including the following steps:
(1) dissolving a suitable precipitant (such as sodium hydroxide, potassium hydroxide, sodium carbonate, sodium bicarbonate, sodium oxalate, ammonia water, ammonium carbonate, urea, or ammonium bicarbonate) with an appropriate amount of a solvent (such as deionized water) to obtain a solution with 1 mol/L to 5 mol/L of the precipitant by concentration, and stirring the solution in a magnetic stirrer for a period of time to obtain a first solution A;
(2) dissolving a Cu salt (such as copper nitrate, copper sulfate, copper chloride, and copper citrate) and a Zn salt (such as zinc nitrate, zinc sulfate, zinc acetate, and zinc chloride) with an appropriate amount of a solvent (such as deionized water), stirring a resulting solution in the magnetic stirrer for 20 min to obtain a second solution B1 with copper and zinc at a molar ratio of less than 0.05:1;
(3) dissolving a Ga salt (such as gallium nitrate, gallium sulfate, gallium acetate, and gallium chloride) and the Zn salt (such as zinc nitrate, zinc sulfate, zinc acetate, and zinc chloride) with an appropriate amount of a solvent (such as deionized water), stirring a resulting solution in the magnetic stirrer for 20 min to obtain another second solution B2 with gallium and zinc at a molar ratio of less than 0.1:1;
(4) subjecting the first solution A and the second solution B to precipitation or hydrolysis at 50° C. to 90° C. to obtain a precipitate, and washing and drying the precipitate to obtain a precursor sample; and
(5) conducting calcination on the precursor sample at 300° C. to 500° C. for 3 h to 5 h to obtain a Cu-doped ZnO catalyst or a Ga-doped ZnO catalyst.

In another aspect of the present disclosure, a synthesis method is provided for preparing a higher alcohol using a doped ZnO catalyst; and the doped ZnO catalyst used in the preparation method is prepared by the preparation method of a ZnO catalyst, including the following steps: subjecting the doped ZnO catalyst to grinding, tabletting, crushing, and sieving, packing in a fixed bed while fixing in a position with a filler, conducting reduction in a hydrogen atmosphere on the doped ZnO catalyst, and conducting the hydrogenation of CO on the fixed bed at 4 MPa to 6 MPa and 200° C. to 400° C. with a gas hourly space velocity (GHSV) of 3,000 $h^{-1}$ to 9,000 $h^{-1}$ and a $H_2$/CO of 1 to 2.

After a stable catalytic reaction, the catalyst has a CO conversion rate of 10% to 70%, and the higher alcohol accounts for greater than 40% of an obtained product.

In an example of the present disclosure, the synthesis method of a higher alcohol by hydrogenation of CO on a fixed bed using a doped ZnO catalyst has a high proportion of the higher alcohols, a desirable catalyst activity, a simple process, and broad industrial prospects.

DETAILED DESCRIPTION OF THE EMBODIMENTS

The technical solutions of the present disclosure are described in further detail below with reference to examples. The following description of the embodiments of the present disclosure with reference to the accompanying drawings is intended to explain the general conception of the present disclosure, but should not be construed as a limitation on the present disclosure.

In the background, the shortcomings of Cu-doped ZnO catalyst are discussed. One is that Cu has a doping amount of not less than 5 wt %, and its catalytic product is mainly methanol, while it is hoped that more higher alcohols can be obtained; two is that in order to obtain more higher alcohols, at least one Fischer-Tropsch element is generally used on the basis of a zinc-copper component.

In view of this, the present disclosure provides a preparation method of a doped ZnO catalyst, where the doped ZnO catalyst is used to synthesize a higher alcohol by hydrogenation of CO on a fixed bed; and the preparation method includes the following steps:
mixing a precipitant and a first solvent to form a first solution having 1 mol/L to 5 mol/L of the precipitant by concentration;
mixing one of a Cu salt or a Ga salt, a Zn salt, and a second solvent to form a second solution having Cu and Zn at a molar ratio of less than 0.05:1 and Ga and Zn at a molar ratio of less than 0.1:1;
subjecting the first solution and the second solution to precipitation or hydrolysis at 50° C. to 90° C. to obtain a precipitate, and washing and drying the precipitate to obtain a precursor sample; and
conducting calcination on the precursor sample at 300° C. to 500° C. for 3 h to 5 h to obtain a Cu-doped ZnO catalyst or a Ga-doped ZnO catalyst.

In an example, the precipitant is any one or a combination of two or more selected from the group consisting of sodium hydroxide, potassium hydroxide, sodium carbonate, sodium bicarbonate, sodium oxalate, ammonia water, ammonium carbonate, urea, and ammonium bicarbonate.

In another example, the Cu salt is any one or a combination of two or more selected from the group consisting of copper nitrate, copper sulfate, copper chloride, and copper citrate; or the Ga salt is any one or a combination of two or more selected from the group consisting of gallium nitrate, gallium sulfate, gallium acetate, and gallium chloride. Optionally, the Zn salt is any one or a combination of two or more selected from the group consisting of zinc nitrate, zinc sulfate, zinc acetate, and zinc chloride. At least one of the first solvent and the second solvent includes deionized water.

It should be understood that the precipitant, the Cu salt, the Ga salt, and the Zn salt only show some common examples and are not exhaustive examples.

In a further example, Cu and Zn have a molar ratio of (0.01-0.04):1 (such as 0.01:1, 0.02:1, 0.03:1, or 0.04:1), and Ga and Zn have a molar ratio of (0.01-0.1):1 (such as 0.01:1, 0.03:1, 0.05:1, 0.07:1, or 0.1:1).

In some examples, the precipitant is dissolved in the first solvent, and stirred, for example, in a magnetic stirrer, to form the first solution; and one of the Cu salt or the Ga salt, and the Zn salt are dissolved in the second solvent, and stirred in the magnetic stirrer to form the second solution.

It should be understood that the preparation method includes co-precipitation or hydrothermal synthesis, and of course any other known suitable method can also be used.

In addition, the present disclosure further provides a synthesis method of a higher alcohol using a doped ZnO catalyst, where the doped ZnO catalyst is prepared by the preparation method above; and the synthesis method of a higher alcohol using the doped ZnO catalyst by hydrogenation of CO on a fixed bed includes the following steps:

subjecting the doped ZnO catalyst to grinding, tabletting, crushing, and sieving, packing in the fixed bed while fixing in a position with a filler, conducting reduction in a hydrogen atmosphere on the doped ZnO catalyst, and conducting the hydrogenation of CO on the fixed bed at 4 MPa to 6 MPa and 200° C. to 400° C. (optionally 250° C. to 320° C.) with a GHSV of 3,000 $h^{-1}$ to 9,000 $h^{-1}$ (optionally 5,000 $h^{-1}$ to 8,000 $h^{-1}$) and a $H_2/CO$ of 1 to 2.

In some examples, after a stable catalytic reaction, the doped ZnO catalyst has a CO conversion rate of 10% to 70%, and the higher alcohol accounts for greater than 40% of an obtained product.

The following only shows a part of the examples of the present disclosure, which are only used for exemplary illustration; those skilled in the art can understand other feasible examples of the present disclosure, which will not be repeated herein.

Example 1

Zinc nitrate was dissolved in 200 mL of deionized water, and copper nitrate was added; and a resulting solution was subjected to magnetic stirring for 20 min to form a copper-zinc salt solution with n (Cu) and n (Zn) at a ratio of 0.01:1;

1.6 M of sodium carbonate was dissolved in 200 mL of the deionized water, and subjected to magnetic stirring for 20 min; and a resulting solution was heated in a water bath to 20° C. to form a sodium carbonate solution;

the sodium carbonate solution and the copper-zinc salt solution were added dropwise to a reaction vessel (such as a three-necked flask) while maintaining a pH value of 6.5, and continuously stirred to form a uniform and stable precipitate at 65° C.; and the precipitate was aged (such as for 6 h), and then subjected to suction filtration and washing to obtain a treated precipitate;

the treated precipitate was dried at 100° C. overnight to obtain a precursor sample; and the precursor sample was subjected to calcination in a muffle furnace at 330° C. for 3 h to obtain a Cu-doped ZnO catalyst; and the Cu-doped ZnO catalyst was subjected to grinding, tabletting, crushing, and sieving to obtain catalyst particles of 40 mesh to 60 mesh, and the Cu-doped ZnO catalyst particles were packed into a fixed bed reactor and fixed with a filler; the Cu-doped ZnO catalyst was reduced under a $H_2$ atmosphere, and then reacted at 4 MPa and 300° C. with a GHSV of 6,000 $h^{-1}$ and a $H_2/CO$ of 1 for activity evaluation. The reactivity evaluation results were shown in Table 1, and a proportion of the higher alcohol was a percentage of a C2+ alcohol in an alcohol product.

Example 2

Zinc nitrate was dissolved in 200 mL of deionized water, and copper nitrate was added; and a resulting solution was subjected to magnetic stirring for 20 min to form a copper-zinc salt solution with n (Cu) and n (Zn) at a ratio of 0.04:1;

3 mol/L of urea was dissolved in 200 mL of the deionized water, and subjected to magnetic stirring for 20 min; and a resulting solution was heated in a water bath to 20° C. to form a urea solution;

the copper-zinc salt solution and the urea solution were mixed to form a uniform and stable solution, heated in water bath at 90° C. for 8 h, and subjected to suction filtration and washing to obtain a precipitate;

the treated precipitate was dried at 100° C. overnight to obtain a precursor sample; and the precursor sample was subjected to calcination in a muffle furnace at 330° C. for 3 h to obtain a Cu-doped ZnO catalyst; and the Cu-doped ZnO catalyst was subjected to grinding, tabletting, crushing, and sieving to obtain catalyst particles of 40 mesh to 60 mesh, and the Cu-doped ZnO catalyst particles were packed into a fixed bed reactor and fixed with a filler; the Cu-doped ZnO catalyst was reduced under a $H_2$ atmosphere, and then reacted at 4 MPa and 290° C. with a GHSV of 6,000 $h^{-1}$ and a $H_2/CO$ of 2 for activity evaluation. The reactivity evaluation results were shown in Table 1, and a proportion of the higher alcohol was a percentage of a C2+ alcohol in an alcohol product.

Example 3

Zinc nitrate was dissolved in 200 mL of deionized water, and gallium nitrate was added; and a resulting solution was subjected to magnetic stirring for 20 min to form a gallium-zinc salt solution with n (Ga) and n (Zn) at a ratio of 0.01:1;

1.6 M of sodium carbonate was dissolved in 200 mL of the deionized water, and subjected to magnetic stirring for 20 min; and a resulting solution was heated in a water bath to 20° C. to form a sodium carbonate solution;

the sodium carbonate solution and the gallium-zinc salt solution were added dropwise to a three-necked flask while maintaining a pH value of 6.5, and continuously stirred to form a uniform and stable precipitate; and the precipitate was aged (such as for 6 h), and then subjected to suction filtration and washing to obtain a treated precipitate;

the treated precipitate was dried at 100° C. overnight to obtain a precursor sample; and the precursor sample was subjected to calcination in a muffle furnace at 330° C. for 3 h to obtain a Ga-doped ZnO catalyst; and the Ga-doped ZnO catalyst was subjected to grinding, tabletting, crushing, and sieving to obtain catalyst particles of 40 mesh to 60 mesh, and the Ga-doped ZnO catalyst particles were packed into a fixed bed reactor and fixed with a filler; the Ga-doped ZnO catalyst was reduced under a $H_2$ atmosphere, and then reacted at 4 MPa and 280° C. with a GHSV of 6,000 $h^{-1}$ and a $H_2$/CO of 2 for activity evaluation. The reactivity evaluation results were shown in Table 1, and a proportion of the higher alcohol was a percentage of a C2+ alcohol in an alcohol product.

Example 4

Zinc nitrate was dissolved in 200 mL of deionized water, and gallium nitrate was added; and a resulting solution was subjected to magnetic stirring for 20 min to form a gallium-zinc salt solution with n (Ga) and n (Zn) at a ratio of 0.04:1;

3 mol/L of urea was dissolved in 200 mL of the deionized water, and subjected to magnetic stirring for 20 min; and a resulting solution was heated in a water bath to 20° C. to form a urea solution;

the gallium-zinc salt solution and the urea solution were mixed to form a uniform and stable solution, heated in water bath at 90° C. for 8 h, and then subjected to suction filtration and washing to obtain a treated precipitate; the treated precipitate was dried at 100° C. overnight to obtain a precursor sample; and the precursor sample was subjected to calcination in a muffle furnace at 330° C. for 3 h to obtain a Ga-doped ZnO catalyst; and the Ga-doped ZnO catalyst was subjected to grinding, tabletting, crushing, and sieving to obtain catalyst particles of 40 mesh to 60 mesh, and the Ga-doped ZnO catalyst particles were packed into a fixed bed reactor and fixed with a filler; the Ga-doped ZnO catalyst was reduced under a $H_2$ atmosphere, and then reacted at 4 MPa and 300° C. with a GHSV of 8,000 $h^{-1}$ and a $H_2$/CO of 1 for activity evaluation. The reactivity evaluation results were shown in Table 1, and a proportion of the higher alcohol was a percentage of a C2+ alcohol in an alcohol product.

TABLE 1

Evaluation results of reactivity of catalysts in Examples 1 to 4

| Example | CO conversion rate (%) | Proportion of higher alcohol (%) |
|---|---|---|
| 1 | 62.84 | 46.08 |
| 2 | 18.06 | 69.89 |
| 3 | 15.75 | 65.78 |
| 4 | 16.23 | 55.31 |

In the examples of the present disclosure, at least one advantage described in the following aspects are achieved: the ZnO is used as a main component of the catalyst, and a small amount of copper or gallium is doped to enhance an interaction between the ZnO or the Cu or Ga;

the Cu-doped ZnO catalyst has an extremely low metal content (<0.05 mol), and the Ga-doped ZnO catalyst has a gallium content of less than 0.1 mol, without any additives and Fischer-Tropsch elements;

the Cu-doped ZnO catalyst or the Ga-doped ZnO catalyst exhibits a desirable activity and an excellent proportion of the higher alcohols in hydrogenation of CO; and the Cu-doped ZnO catalyst or the Ga-doped ZnO catalyst is prepared by co-precipitation or hydrothermal synthesis.

Although some examples of the present general inventive concept have been shown and described, those of ordinary skill in the art will appreciate that changes may be made to these examples without departing from the principles and spirit of the present general inventive concept. The scope of the present disclosure is defined by the claims and their equivalents.

What is claimed is:

1. A preparation method of a doped ZnO catalyst, wherein the doped ZnO catalyst is used to synthesize a higher alcohol by hydrogenation of CO on a fixed bed; and the preparation method consists of the following steps:

mixing a precipitant and a first solvent to form a first solution having 1 mol/L to 5 mol/L of the precipitant by concentration;

mixing one of a Cu salt and a Ga salt, a Zn salt, and a second solvent to form a second solution having Cu and Zn at a molar ratio of less than 0.05:1 or Ga and Zn at a molar ratio of less than 0.1:1;

subjecting the first solution and the second solution to precipitation or hydrolysis at 50° C. to 90° C. to obtain a precipitate, and washing and drying the precipitate to obtain a precursor sample; and conducting calcination on the precursor sample at 300° C. to 500° C. for 3 h to 5 h to obtain a Cu-doped ZnO catalyst or a Ga-doped ZnO catalyst.

2. The preparation method of a doped ZnO catalyst according to claim 1, wherein the precipitant is any one or a combination of two or more selected from the group consisting of sodium hydroxide, potassium hydroxide, sodium carbonate, sodium bicarbonate, sodium oxalate, ammonia water, ammonium carbonate, urea, and ammonium bicarbonate.

3. The preparation method of a doped ZnO catalyst according to claim 2, wherein the Cu salt is any one or a combination of two or more selected from the group consisting of copper nitrate, copper sulfate, copper chloride, and copper citrate; and the Ga salt is any one or a combination of two or more selected from the group consisting of gallium nitrate, gallium sulfate, gallium acetate, and gallium chloride.

4. The preparation method of a doped ZnO catalyst according to claim 3, wherein

Cu and Zn have a molar ratio of (0.01-0.04):1, and Ga and Zn have a molar ratio of (0.01-0.1):1.

5. The preparation method of a doped ZnO catalyst according to claim 4, wherein the Zn salt is any one or a combination of two or more selected from the group consisting of zinc nitrate, zinc sulfate, zinc acetate, and zinc chloride.

6. The preparation method of a doped ZnO catalyst according to claim 5, wherein at least one of the first solvent and the second solvent comprises deionized water.

7. The preparation method of a doped ZnO catalyst according to claim 6, wherein:

the first solution is prepared by dissolving the precipitant in the first solvent, and stirring in a magnetic stirrer to form the first solution; and the second solution is prepared by dissolving one of the Cu salt and the Ga salt, and the Zn salt in the second solvent, and stirring in the magnetic stirrer to form the second solution.

8. The preparation method of a doped ZnO catalyst according to claim 5, wherein:
the first solution is prepared by dissolving the precipitant in the first solvent, and stirring in a magnetic stirrer to form the first solution; and
the second solution is prepared by dissolving one of the Cu salt and the Ga salt, and the Zn salt in the second solvent, and stirring in the magnetic stirrer to form the second solution.

9. The preparation method of a doped ZnO catalyst according to claim 4, wherein:
the first solution is prepared by dissolving the precipitant in the first solvent, and stirring in a magnetic stirrer to form the first solution; and
the second solution is prepared by dissolving one of the Cu salt and the Ga salt, and the Zn salt in the second solvent, and stirring in the magnetic stirrer to form the second solution.

10. The preparation method of a doped ZnO catalyst according to claim 3, wherein:
the first solution is prepared by dissolving the precipitant in the first solvent, and stirring in a magnetic stirrer to form the first solution; and
the second solution is prepared by dissolving one of the Cu salt and the Ga salt, and the Zn salt in the second solvent, and stirring in the magnetic stirrer to form the second solution.

11. The preparation method of a doped ZnO catalyst according to claim 2, wherein:
the first solution is prepared by dissolving the precipitant in the first solvent, and stirring in a magnetic stirrer to form the first solution; and
the second solution is prepared by dissolving one of the Cu salt and the Ga salt, and the Zn salt in the second solvent, and stirring in the magnetic stirrer to form the second solution.

12. The preparation method of a doped ZnO catalyst according to claim 1, wherein:
the first solution is prepared by dissolving the precipitant in the first solvent, and stirring in a magnetic stirrer to form the first solution; and
the second solution is prepared by dissolving one of the Cu salt and the Ga salt, and the Zn salt in the second solvent, and stirring in the magnetic stirrer to form the second solution.

13. The preparation method of a doped ZnO catalyst according to claim 12, wherein
the doped ZnO catalyst is prepared by co-precipitation or hydrothermal synthesis.

14. A synthesis method of a higher alcohol using a doped ZnO catalyst, wherein the doped ZnO catalyst is prepared by the preparation method according to claim 1; and the synthesis method of a higher alcohol using the doped ZnO catalyst by hydrogenation of CO on a fixed bed comprises the following steps:
subjecting the doped ZnO catalyst to grinding, tableting, crushing, and sieving, packing in the fixed bed while fixing in a position with a filler, conducting reduction on the doped ZnO catalyst, and conducting the hydrogenation of CO on the fixed bed at 4 Mpa to 6 Mpa and 200° C. to 400° C. with a gas hourly space velocity (GHSV) of 3,000 $h^{-1}$ to 9,000 $h^{-1}$ and a $H_2$/CO of 1 to 2.

15. The synthesis method of a higher alcohol using a doped ZnO catalyst according to claim 14, wherein
the precipitant is any one or a combination of two or more selected from the group consisting of sodium hydroxide, potassium hydroxide, sodium carbonate, sodium bicarbonate, sodium oxalate, ammonia water, ammonium carbonate, urea, and ammonium bicarbonate.

16. The synthesis method of a higher alcohol using a doped ZnO catalyst according to claim 15, wherein
the Cu salt is any one or a combination of two or more selected from the group consisting of copper nitrate, copper sulfate, copper chloride, and copper citrate; and
the Ga salt is any one or a combination of two or more selected from the group consisting of gallium nitrate, gallium sulfate, gallium acetate, and gallium chloride.

17. The synthesis method of a higher alcohol using a doped ZnO catalyst according to claim 16, wherein
Cu and Zn have a molar ratio of (0.01-0.04):1, and Ga and Zn have a molar ratio of (0.01-0.1):1.

18. The synthesis method of a higher alcohol using a doped ZnO catalyst according to claim 17, wherein
the Zn salt is any one or a combination of two or more selected from the group consisting of zinc nitrate, zinc sulfate, zinc acetate, and zinc chloride.

19. The synthesis method of a higher alcohol using a doped ZnO catalyst according to claim 18, wherein
at least one of the first solvent and the second solvent comprises deionized water.

20. The synthesis method of a higher alcohol using a doped ZnO catalyst according to claim 14, wherein
the doped ZnO catalyst is reduced in a hydrogen atmosphere; and
after a stable catalytic reaction, the doped ZnO catalyst has a CO conversion rate of 10% to 70%, and the higher alcohol accounts for greater than 40% of an obtained product.

* * * * *